US008965489B2

(12) United States Patent
Ghosh (10) Patent No.: US 8,965,489 B2
(45) Date of Patent: Feb. 24, 2015

(54) METHOD AND DETERMINATION OF CARDIAC ACTIVATION FROM ELECTROGRAMS WITH MULTIPLE DEFLECTIONS

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/773,030

(22) Filed: Feb. 21, 2013

(65) Prior Publication Data

US 2014/0235987 A1 Aug. 21, 2014

(51) Int. Cl.
*A61B 5/04* (2006.01)
*A61B 5/046* (2006.01)
*A61B 5/042* (2006.01)
*A61B 5/0432* (2006.01)
*A61B 5/044* (2006.01)
*A61B 5/00* (2006.01)
*A61B 5/0456* (2006.01)

(52) U.S. Cl.
CPC ............ *A61B 5/046* (2013.01); *A61B 5/04012* (2013.01); *A61B 5/0422* (2013.01); *A61B 5/0432* (2013.01); *A61B 5/044* (2013.01); *A61B 5/7239* (2013.01); *A61B 5/0456* (2013.01)
USPC ........................................................ 600/509

(58) Field of Classification Search
None
See application file for complete search history.

(56) References Cited

U.S. PATENT DOCUMENTS

| 5,687,737 | A | * | 11/1997 | Branham et al. | 600/523 |
| 2009/0112109 | A1 | | 4/2009 | Kuklik et al. | |
| 2010/0217144 | A1 | * | 8/2010 | Brian | 600/523 |
| 2012/0283587 | A1 | | 11/2012 | Gosh et al. | |

FOREIGN PATENT DOCUMENTS

EP 1178855 B1 8/2006

OTHER PUBLICATIONS

Konings et al., Configuration of Unipolar Atrial Electrograms During Electrically Induced Atrial Fibrillation in Humans, Circulation. 1997; 95: 1231-1241.
Gaita et al., Different Patterns of Atrial Activation in Idiopathic Atrial Fibrillation: Simultaneous Multisite Atrial Mapping in Patients With Paroxysmal and Chronic Atrial Fibrillation, Journal of the American College of Cardiology, vol. 37, No. 2, 2001, pp. 1-8.

(Continued)

*Primary Examiner* — Christopher D Koharski
*Assistant Examiner* — Elizabeth K So
(74) *Attorney, Agent, or Firm* — Christopher & Weisberg, P.A.

(57) ABSTRACT

A method and system for determining activation times for electric potentials from complex electrograms to identify the location of arrhythmic sources or drivers. The method includes counting a number deflections in a recorded cardiac electrogram signal from at least one electrode for a predetermined amount of time. A deflection time is identified for each of the counted number of deflections. A most negative slope is identified between each of the identified deflections times. Each of the identified most negative slopes is correlated to a possible activation time. Each possible activation time is associated with a corresponding electrode from the at least one electrode. A spatial voltage gradient at each corresponding electrode is calculated for each possible activation time. The greatest spatial voltage gradient is identified. The greatest spatial voltage gradient is correlated to an activation time.

8 Claims, 6 Drawing Sheets

(56) References Cited

OTHER PUBLICATIONS

Punske et al., Spatial Methods of Epicardial Activation Time Determination in Normal Hearts, Annals of Biomedical Engineering, vol. 31, pp. 781-792, 2003.

Ravelli et al., Wave Similarity Mapping Shows the Spatiotemporal Distribution of FibrillatoryWave Complexity in the Human Right Atrium During Paroxysmal and Chronic Atrial Fibrillation, J Cardiovasc Electrophysiol, vol. 16, pp. 1071-1076, Oct. 2005.

Narayan et al., Computational Mapping Identifies Localized Mechanisms for Ablation of Atrial Fibrillation, PLOS ONE, Sep. 2012 | vol. 7 | Issue 9, pp. 1-8.

Lalani et al., Atrial Conduction Slows Immediately Before the Onset of Human Atrial Fibrillation, Journal of the American College of Cardiology, vol. 59, No. 6, 2012, Feb. 7, 2012:595-606.

International Search Report and Written Opinion dated Apr. 2, 2014 for International Application Serial No. PCT/US2014/010841, International Filing Date: Jan. 9, 2014 consisting of 7 pages.

* cited by examiner

METHOD AND DETERMINATION OF CARDIAC ACTIVATION FROM ELECTROGRAMS WITH MULTIPLE DEFLECTIONS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method for determining cardiac activation times from complex electrograms to identify the location of arrhythmic sources.

BACKGROUND OF THE INVENTION

The long term success of treating arrhythmias often depends on the determination of the exact tissue or trigger in the heart causing the arrhythmia so that the malfunctioning tissue can be ablated and the normal rhythm of the heart restored. Ablation of arrhythmias, like atrial fibrillation, whether paroxysmal or chronic, typically involves the simultaneous mapping of a region of cardiac tissue with a multi-electrode catheter in order to identify and ablate tissue sources or drivers of arrhythmias. Maps of cardiac activation often include an electrogram signal recording displaying a progression of electrode depolarizations in the target tissue region in order to identify cardiac activation times to determine arrhythmic sites. The activation times of the electrode depolarizations are often determined by visual analysis of the electrogram, which includes looking for the tallest peak or steepest valley of deflections or the time of zero-crossing for a bipolar or near-field electrogram, or looking for the timing of the most negative slope for a unipolar or far field electrogram.

However, in complex electrograms, as in those in patients with atrial fibrillation, each depolarization may include several non-discrete deflections making an accurate determination of cardiac activation times cumbersome and ambiguous. Thus, current methods and systems of determining activation times are inaccurate thereby reducing the accuracy of atrial fibrillation treatments.

SUMMARY OF THE INVENTION

The present invention advantageously provides a method and system for determining activation times for electric potentials from complex electrograms to identify the location of arrhythmic sources or drivers. The method includes counting a number deflections in a recorded cardiac electrogram signal from at least one electrode for a predetermined amount of time. A deflection time is identified for each of the counted number of deflections. A most negative slope is identified between each of the identified deflections times. Each of the identified most negative slopes is correlated to a possible activation time. Each possible activation time is associated with a corresponding electrode from the at least one electrode. A spatial voltage gradient at each corresponding electrode is calculated for each possible activation time. The greatest spatial voltage gradient is identified. The greatest spatial voltage gradient is correlated to an activation time.

In another embodiment a medical system includes a medical device including a plurality of electrodes. A control unit in communication with the plurality of electrodes is included, the control unit is operable to: transmit radiofrequency energy between the plurality of electrodes when the plurality of electrodes is positioned proximate a target tissue region; record an electrogram signal from the plurality of electrodes proximate the target tissue region; count a number of deflections in the recorded electrogram signal for a predetermined amount of time; identify a deflection time for each of the counted number of deflections; identify a most negative slope between each of the identified deflections times; correlate each of the identified most negative slopes to a possible activation time; associate each possible activation time to a corresponding electrode from the plurality of electrodes; calculate a spatial voltage gradient at each corresponding electrode for each possible activation time; identify the greatest spatial voltage gradient; and correlate the greatest spatial voltage gradient to an activation time.

In yet another embodiment, a medical system includes a medical device including a plurality of electrodes spaced substantially equidistant from an adjacent electrode. A control unit in communication with the plurality of electrodes is included, the control unit is operable to: transmit radiofrequency energy between the plurality of electrodes when the plurality of electrodes are positioned proximate cardiac tissue; record an electrogram signal from the plurality of electrodes proximate the target tissue region; count a number of deflections with a negative slope in the recorded electrogram signal for a predetermined amount of time; identify a deflection time for each of the counted number of deflections; identify a most negative slope between each of the identified deflections times; correlate each of the identified most negative slopes to a possible activation time; associate each possible activation time to a corresponding electrode from the plurality of electrodes; calculate a spatial voltage gradient at each corresponding electrode for each possible activation time; identify the greatest spatial voltage gradient; and correlate the greatest spatial voltage gradient to an activation time.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
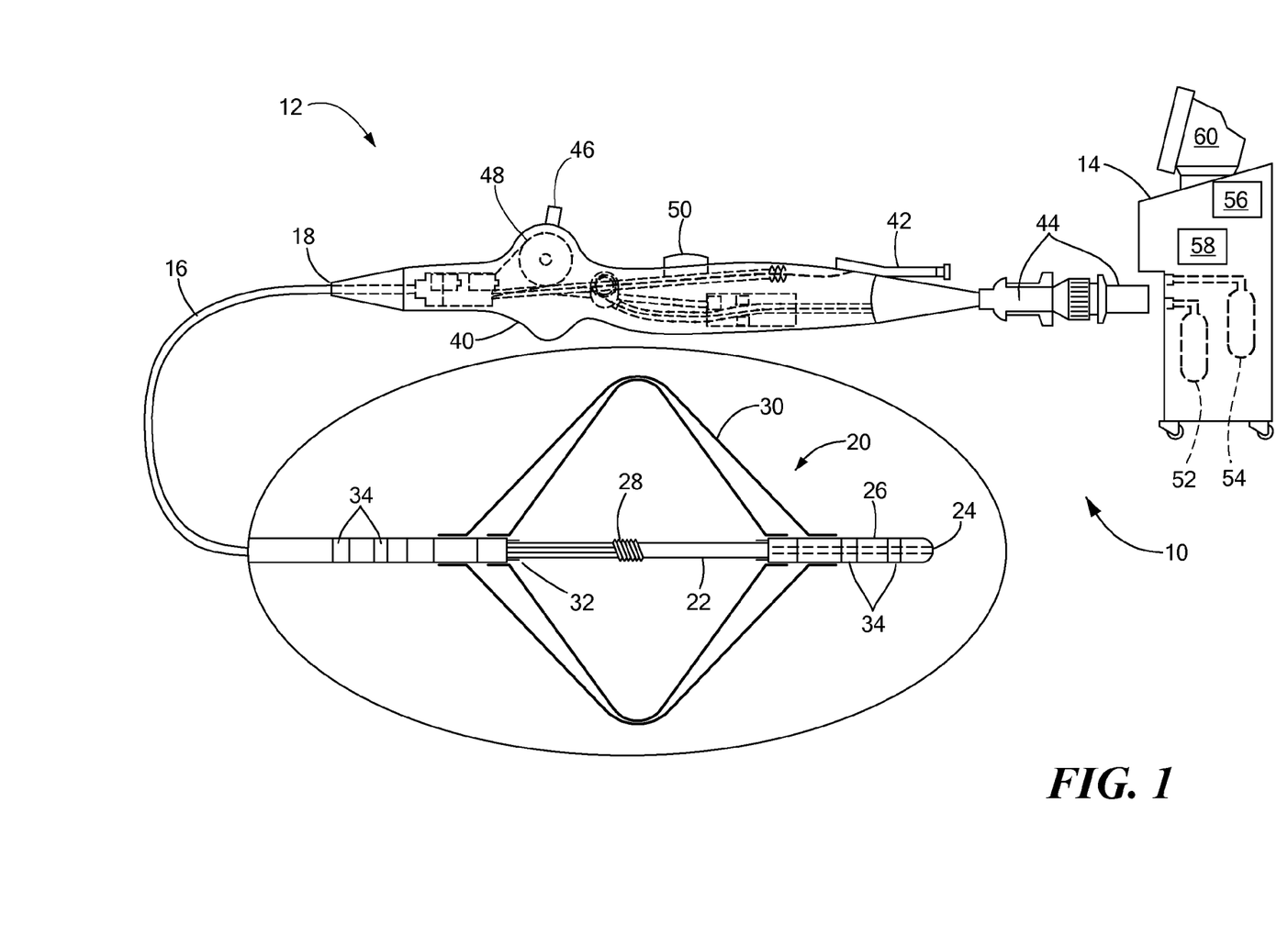
FIG. 1 is an illustration of an example of a medical system constructed in accordance with the principles of the present invention.

The present invention advantageously provides a system and methods of use thereof for determining cardiac activation times in electrograms with complex deflections for patients with arrhythmias. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site or region. The diagnostic or treatment region(s) may deliver, for example, cryogenic therapy, radiofrequency energy, or other energetic transfer with a tissue area in proximity to the treatment region(s), including cardiac tissue.

Now referring to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

Figure 2:
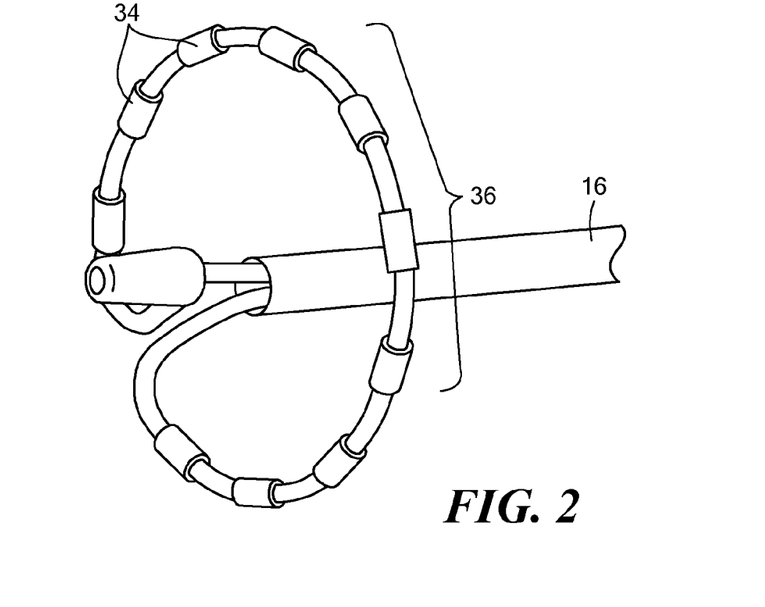
FIG. 2 is an illustration of an example of a medical device assembly constructed in accordance with the principles of the present invention.
Figure 3:
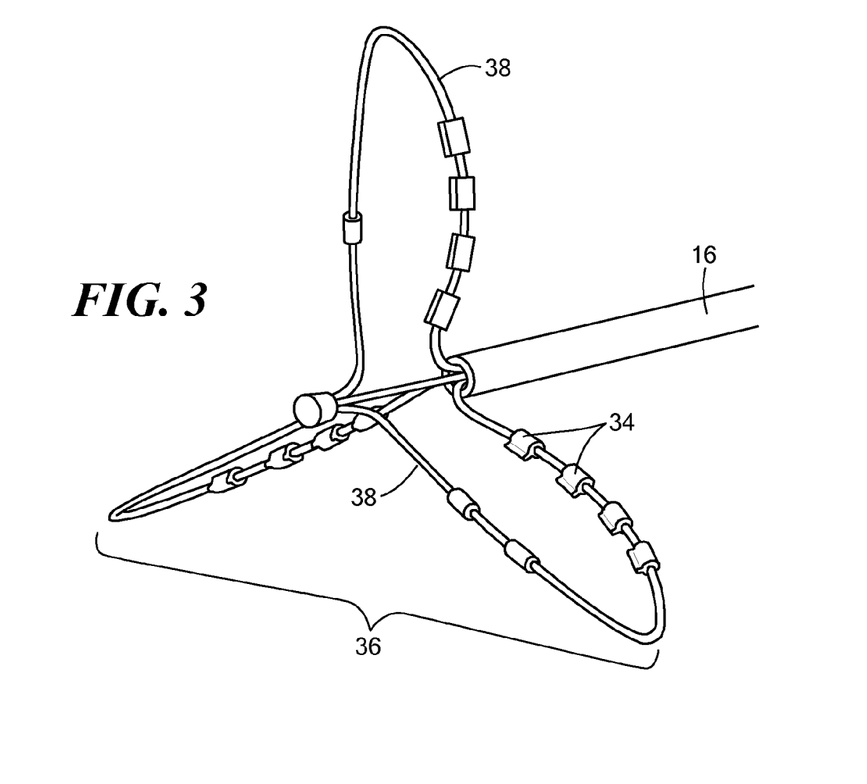
FIG. 3 is another illustration of an example of a medical device assembly constructed in accordance with the principles of the present invention.
Figure 4:
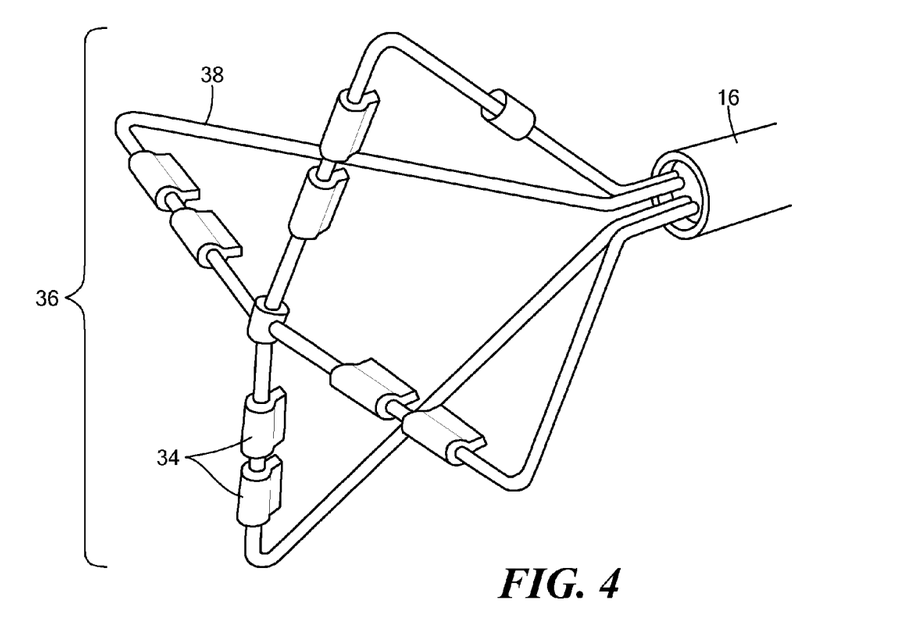
FIG. 4 is still another illustration of an example of a medical device assembly constructed in accordance with the principles of the present invention.
Figure 5:
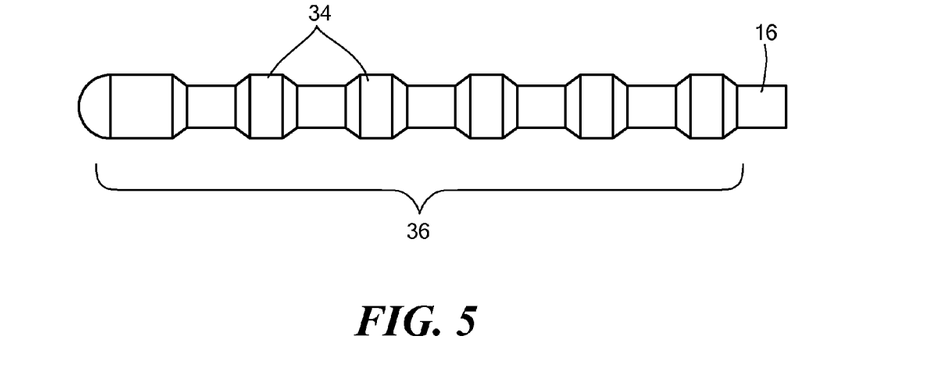
FIG. 5 is yet another illustration of an example of a medical device assembly constructed in accordance with the principles of the present invention.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element. Alternative electrode configurations of the medical device 12 are illustrated in FIGS. 2-5. FIG. 2 includes an electrode array 36 configurable into a looped or substantially circular configuration. The electrode array 36 in FIG. 3 includes a plurality of arms 38, with the electrodes 34 positioned in a proximal-facing direction or orientation on the arms 38. FIG. 4 also includes a plurality of extendable or deployable arms 38 having a plurality of electrodes 34 in a square-like or "X"-shaped configuration. Turning to FIG. 5, a plurality of electrodes 34 are shown in a substantially linear array 36 extending along a portion of the elongate body 16 of the medical device 12. In each of these embodiments shown in FIGS. 2-5, the electrodes 34 may be positioned on the medical device 12 substantially equidistant from an adjacent electrode 34 in the array or may be variable distances from each adjacent electrode 34.

Each electrode 34 may be electrically coupled to an output portion of a radiofrequency signal generator, and each electrode 34 may also include a sensor, such as a thermocouple, an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24. The handle 40 may also include connectors 44 that are matable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16.

The control 14 unit may include a radiofrequency generator or power source 56 as a treatment or diagnostic mechanism in communication with the electrodes 34 of the medical device 12. The radiofrequency generator 56 may have a plurality of output channels, with each channel coupled to an individual electrode 34. The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode (not shown) spaced apart from the electrodes 34 of the medical device 14, such as on a patient's skin for example, and (iii) a combination of the monopolar and bipolar modes.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The control unit 14 may include one or more controllers, processors, and/or software modules containing instructions or algorithms to provide for the automated operation and performance of the features, sequences, calculations, or procedures described herein. For example, the control unit 14 may include a signal processing unit 58 to measure one or more electrical characteristics between the electrodes 34 of the medical device 12. An excitation current may be applied between one or more of the electrodes 34 on the medical device 12 and/or a patient return electrode, and the resulting voltage, impedance, or other electrical properties of the target tissue region may be measured, for example, in an electrogram, as described in more detail below. The control unit may further include a display 60 to display the various recorded signals and measurement, for example, an electrogram.

Figure 6:
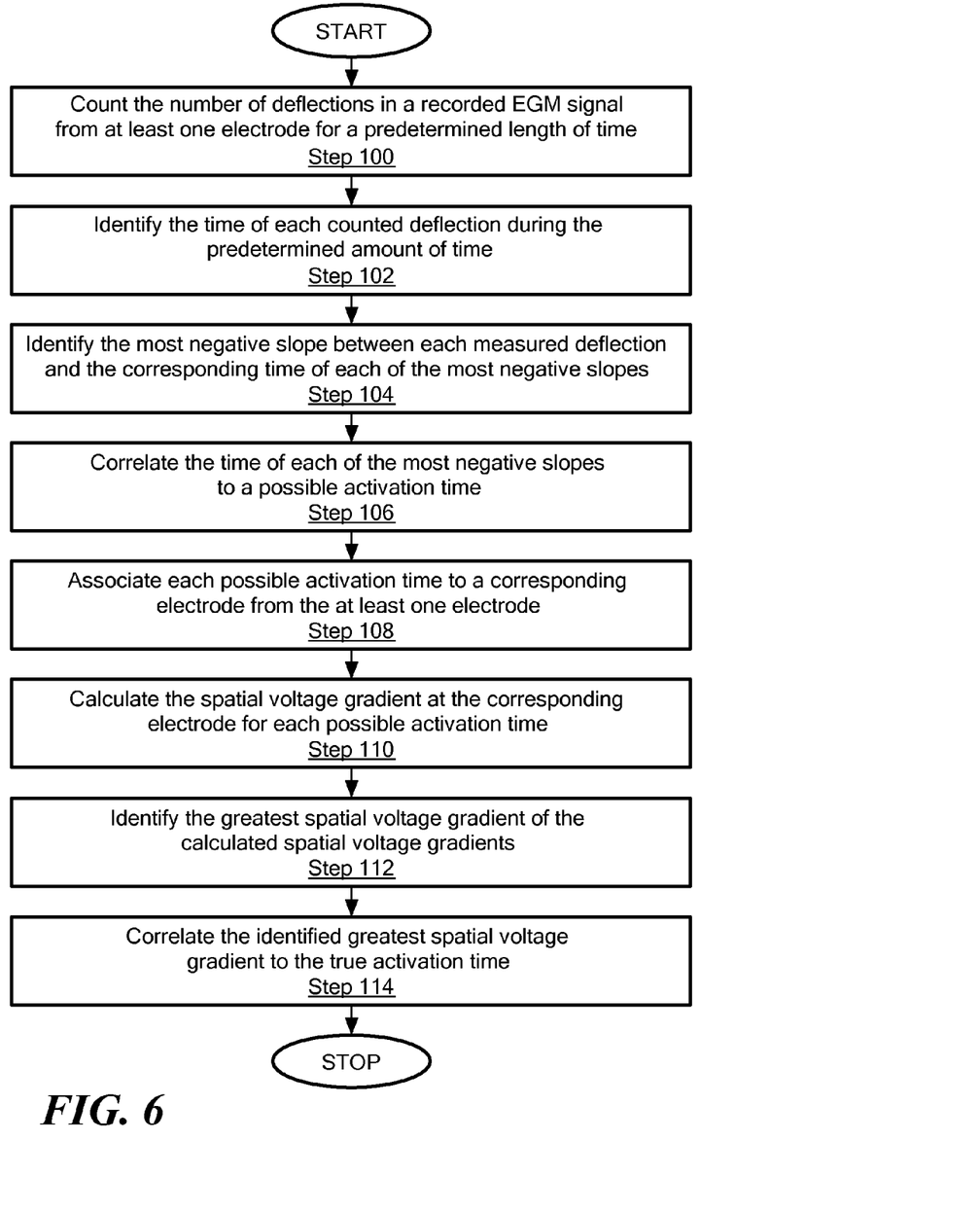
FIG. 6 is a flow chart illustrating an exemplary method of determining cardiac activation times in complex electrograms.

Referring now to FIG. 6, where a flow chart illustrating the various steps of an exemplary method a determining cardiac activation or depolarization times is shown. The method includes providing the medical device 12, for example, any one of the medical devices 12 discussed above, having the plurality of electrodes 34 coupled to the distal portion 20. The plurality of electrodes 34 may be positioned proximate and/or in direct contact with a tissue region to be examined, for example, the myocardium or any portion of the heart. When positioned proximate or in contact with the target tissue region, radiofrequency energy may be transmitted between the plurality of electrodes 34 and/or from at least one of the plurality of electrodes 34 to the reference electrode. An electrogram signal (EGM) may be recorded from the tissue region being examined. For example, an electrocardiogram signal (ECG) may recorded proximate the myocardium. The recorded EGM signal may be in vivo or may be a previously recorded EGM.

Figure 7:
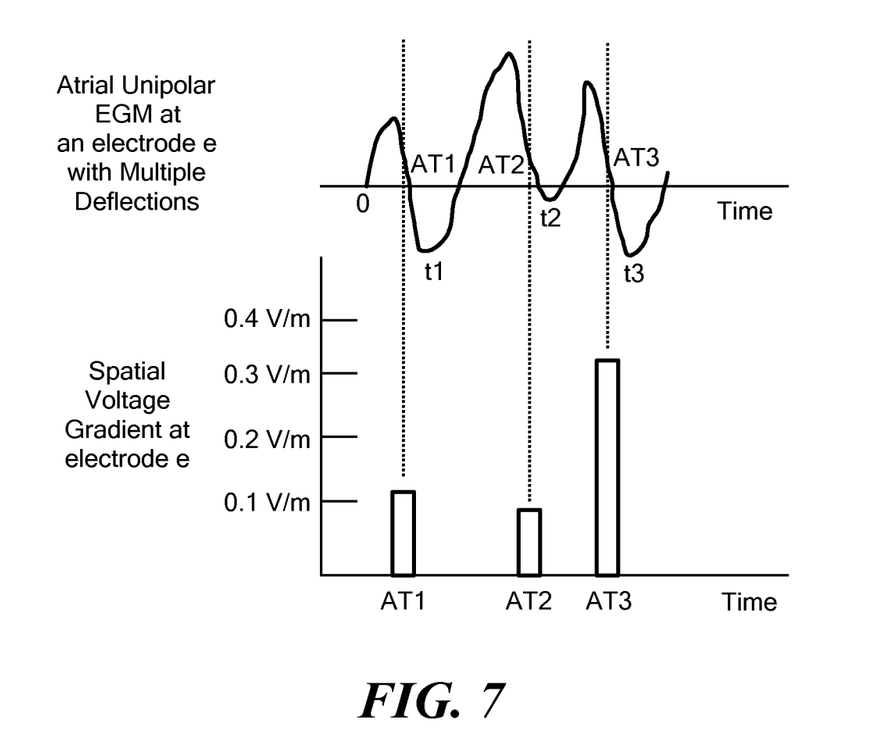
FIG. 7 is a graph showing an exemplary electrogram in which the time of each positive deflection and the possible activation times (top) and the spatial voltage gradient calculated for each possible activation time (bottom) are shown.

Continuing to refer to FIG. 6, the method furthers include counting the number of deflections in the recorded EGM signal from at least one of the plurality of electrodes 30 for a predetermined length of time (Step 100). The number deflections are determined by counting the number of times the slopes of the EGM signal change from positive to negative, or vice-versa, with the signal magnitude at the time-instant above a specified threshold. The counting of the number of deflections may be accomplished through visual analysis or by the control unit 14. The number of deflections may be determined from the number of times the slope of the EGM signal changes sign from negative to positive or zero, and corresponding time-points (at which the slope changes sign in the said direction) define the intervals for determining the most negative slopes. For example, as shown in FIG. 7, the reference designators t1, t2, and t3 represents times when the slope of the recorded EGM changed from negative to positive. The predetermined amount of time may be specified before the EGM is recorded. For example, the predetermined amount of time may be approximately 100 ms to 300 ms or may be substantially equal to the cycle length of a chronic or paroxysmal arrhythmia for a particular patient to be examined, which may be determined before the procedure by the control unit using one of the medical devices 12 discussed above or by other methods known in the art. Alternatively, the predetermined amount of time may be within a specified range of the recorded or in vivo EGM. Alternatively the time-window for analysis may be identified from a surface ECG lead which records signal simultaneously with the electrode array 36. For example, in a 300 ms (T=300 ms) EGM recording, the predetermined amount of time may in the range from T=100 ms to T=300 ms.

The method further includes indentifying the time, for example, t1, t2, t3, . . . tn discussed above, for each measured deflection during the predetermined amount of time (Step 102). For example, if seven deflections are measured, seven different times for each deflection may be identified during the predetermined amount of time. The most negative slope between each measured deflection, and the corresponding time of each of the most negative slopes, is identified (Step 104). For example, the most negative, or steepest, slope may be calculated between intervals 0-t1, t1-t2, t3, . . . tn-1-tn, where t0 is the time-point corresponding to the last deflection identified within the predetermined amount of time and the corresponding time of the most negative slope between each time interval is identified. The slope of the EGM signal may be calculated by the difference between successive samples or other published schemes of numerical differentiation. For example, as shown in FIG. 7, the time of the most negative slope between 0-t1 is identified by the reference designator "AT1." The time of the most negative slope in each interval is the correlated to a possible activation time for the particular tissue being examined (Step 106). In the example shown in FIG. 7, three possible activation times, AT1, AT2, and AT3 are identified. In another example in which the predetermined amount of time is 200 ms with sampling rate of 1000 HZ and with an EGM signal with three deflections, three possible activation times may be identified in Step 106.

Continuing to refer to FIG. 6, each possible activation time may be associated with a corresponding electrode 34 on the medical device 12. (Step 108). In particular, based on the position of the plurality of electrodes 34 during in vivo measurement, or previously correlated EGM signals to a particular electrode 34, the possible activation times may be associated with its corresponding electrode 34. In the example illustrated in FIG. 7, the corresponding electrode 34 is referred to by reference designator "e." The spatial voltage gradient at the corresponding electrode "e" may then be calculated for each possible activation time (Step 110).

Figure 8:
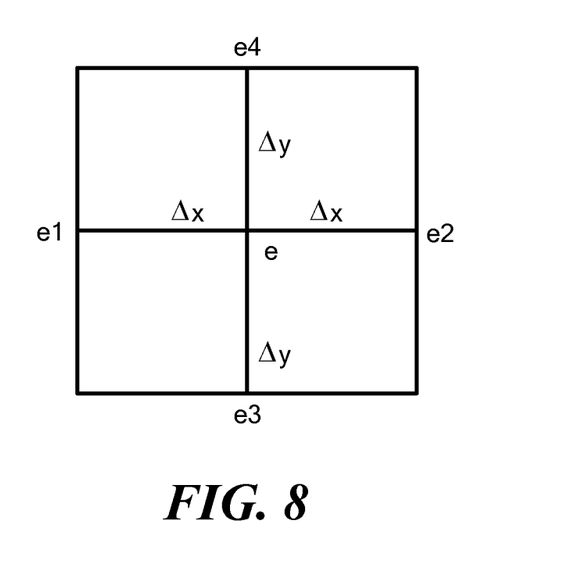
FIG. 8 is a two-dimensional grid showing the spatial arrangement of a plurality of electrodes.

Referring now to FIG. 8, where an exemplary two-dimensional grid is shown illustrating the position of five electrodes e, e1, e2, e3, e4, and e5 in an exemplary method of calculating the spatial voltage gradient when bipolar radiofrequency energy is transmitted between adjacent electrodes. Such a configuration may be achieved, for example, when the medical device 12 in FIG. 4 is applied to a target tissue region. The horizontal spacing between electrodes e1-e and e-e2 is referred to as "$\Delta x$." The vertical spacing between electrodes e3-e and e-e4 is referred to as "$\Delta y$." The central difference method may be use calculate the spatial voltage gradient ($\Delta V_e$ (t)) at electrode e on this exemplary two-dimensional grid by the following equation, where "V" is the voltage:

$$\Delta V_{e,x}(t)=(V_{e2}(t)-V_{e1}(t)/(2\,\Delta x)$$

$$\Delta V_{e,y}(t)=(V_{e4}(t)-V_{e3}(t)/(2\,\Delta y)$$

$$\Delta V_e(t)=\sqrt{(\Delta V_{e,x}^2(t)+\Delta V_{e,y}^2(t))}$$

Other methods are contemplated to calculate $\Delta V_{e,x}(t)$ and $\Delta V_{e,y}(t)$, for example, forward difference or backward difference methods and other gradient operators may be used with different mapping grids depending on the spacing and positions of the electrodes 34, which may depend on the particular medical device.

For each possible activation time at electrode e, for example, AT1, AT2, AT3 the spatial voltage gradient may be calculated and the greatest spatial voltage gradient may be identified (Step 112). For example, as shown in FIG. 6, the spatial voltage gradients at times AT1, AT2, and AT3 were calculated and identified. Possible activation time AT3 was identified as the greatest voltage gradient and then correlated to the true activation time (Step 114).

Figure 9:
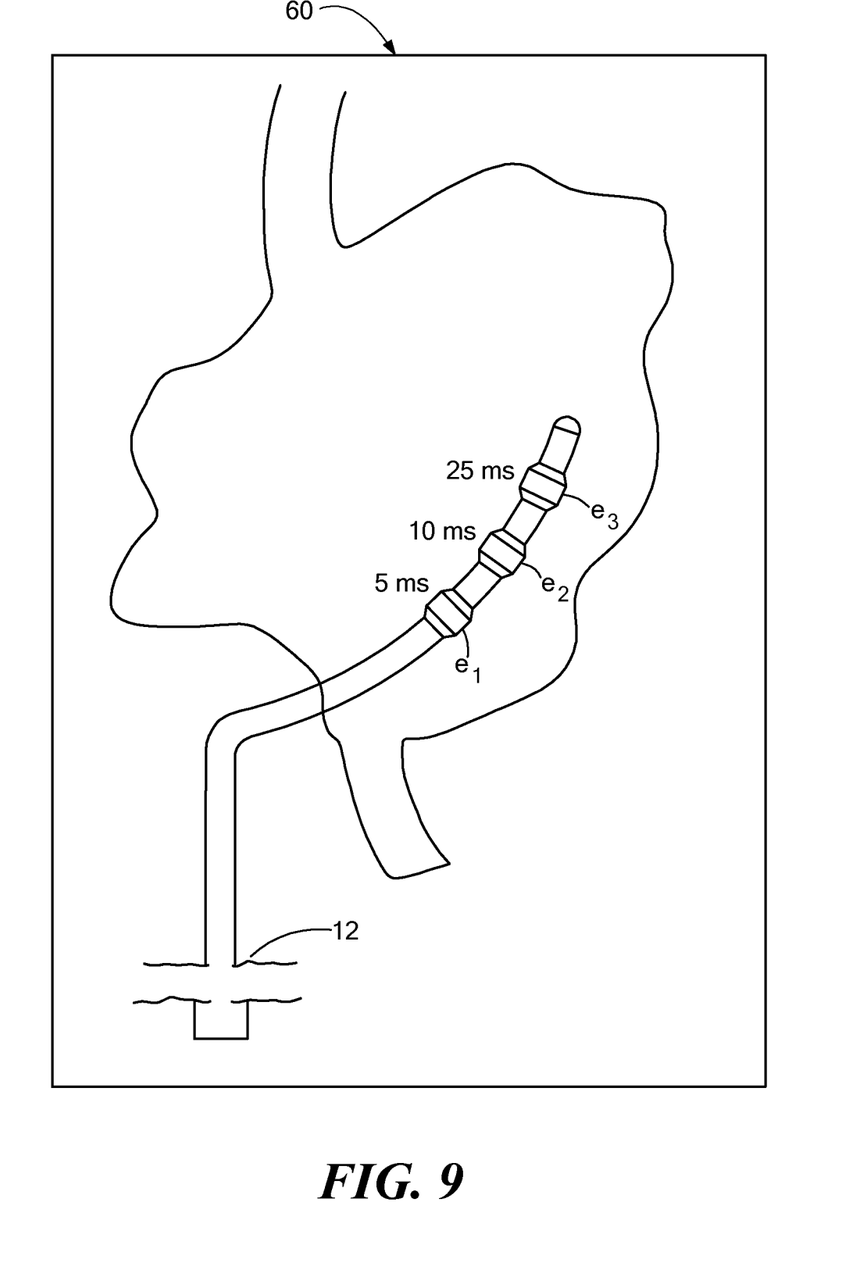
FIG. 9 is an illustration of a display in accordance with the present invention displaying cardiac tissue, a medical device with electrodes, and the activation times associated with each electrode.

Referring now to FIG. 9, where an exemplary display 60 is shown. The medical device 12, for example, the medical device shown in FIG. 5 may be displayed on the display 60 before, during, and/or after the method of determining cardiac activation times described above. In the embodiment shown in FIG. 9, the plurality of electrodes 34, represented by e1, e2, and e3 are shown in contact with a region of the myocardium. As radiofrequency energy is transmitted between the electrodes 34, the control unit 14 may be operable to simultaneously display the position of the electrodes 34, the target tissue region, and the determined cardiac activation times at each respective electrode 34. For example, the display 60 may display an activation time of 5 ms for e1, 10 ms, for e2, and 25 ms for e3 such that the location of arrhythmic focus or substrate may be mapped. It is further contemplated that as the electrodes 34 are repositioned, the control unit 14 may superimpose previously recorded data on the display 60 so that an entire region of the heart may be mapped and visualized with activation times. A color-coded isochronal map of activation times may be constructed from the determined activation times at different electrodes and superimposed on the corresponding anatomic area of the heart to display an electro-anatomic map of cardiac activation during an arrhythmia cycle. Once the malfunctioning tissue substrate is identified, the ablation energy may be transmitted to a particular electrode or electrodes 34 to ablate the damaged tissue and restore the normal rhythm of the heart.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, comprising:
   a medical device including a plurality of electrodes;
   a control unit in communication with the plurality of electrodes, the control unit operable to:
      transmit radiofrequency energy between the plurality of electrodes when the plurality of electrodes is positioned proximate a target tissue region;
      record an electrogram signal from the plurality of electrodes proximate the target tissue region;
      count a number of deflections in the recorded electrogram signal for a predetermined amount of time;
      identify a deflection time for each of the counted number of deflections;
      identify a most negative slope between each of the identified deflections times;
      correlate each of the identified most negative slopes to a possible activation time;
      associate each possible activation time to a corresponding electrode from the plurality of electrodes;
      calculate a spatial voltage gradient at each corresponding electrode for each possible activation time;
      identify the greatest spatial voltage gradient; and
      correlate the greatest spatial voltage gradient to an activation time.

2. The medical system of claim 1, further comprising a display, and wherein the control unit is further operable to:
   display an image of the target tissue region on the display; and display the activation time at target tissue region proximate the electrode at which the activation time is determined.

3. The medical system of claim 1, wherein the counting of the number deflections includes counting the number of deflections with a negative slope.

4. The medical system of claim 1, wherein each of the plurality of electrodes is spaced substantially equidistant from an adjacent electrode.

5. The medical system of claim 1, wherein the target tissue region is the myocardium.

6. The medical system of claim 5, wherein the control unit is further operable to:
   measure a cycle length of an arrhythmia in a patient having atrial fibrillation; and wherein the predetermined amount of time is substantially equal to the cycle length of the arrhythmia.

7. The medical system of claim 1, further comprising a reference electrode remote from the medical device, and wherein the control unit is further operable to transmit both unipolar and bipolar radiofrequency energy.

8. The medical system of claim 1, wherein the medical device includes a plurality of carrier arms, and wherein each carrier arms includes at least two of the plurality of electrodes.

* * * * *